United States Patent
Salo et al.

(10) Patent No.: US 8,571,657 B2
(45) Date of Patent: Oct. 29, 2013

(54) HEART FAILURE THERAPY ADJUSTMENT BASED ON VENTRICULAR PRESSURES

(75) Inventors: Rodney Salo, Fridley, MN (US); Angelo Auricchio, Magdeburg (DE)

(73) Assignee: Cardiac Pacemakers, Inc., St. Paul, MN (US)

(*) Notice: Subject to any disclaimer, the term of this patent is extended or adjusted under 35 U.S.C. 154(b) by 1225 days.

(21) Appl. No.: 12/221,332

(22) Filed: Aug. 1, 2008

(65) Prior Publication Data

US 2008/0300643 A1 Dec. 4, 2008

Related U.S. Application Data

(60) Continuation of application No. 10/745,031, filed on Dec. 23, 2003, now Pat. No. 7,409,224, which is a division of application No. 10/038,936, filed on Jan. 4, 2002, now Pat. No. 6,666,826.

(51) Int. Cl.
A61N 1/37 (2006.01)

(52) U.S. Cl.
USPC .......................................................... 607/18

(58) Field of Classification Search
USPC .................................. 607/6, 17, 18
See application file for complete search history.

(56) References Cited

U.S. PATENT DOCUMENTS

| | | |
|---|---|---|
| 3,995,623 A | 12/1976 | Blake et al. |
| 4,485,813 A | 12/1984 | Anderson et al. |
| 4,674,518 A | 6/1987 | Salo |
| 4,719,921 A | 1/1988 | Chirife |
| 4,773,401 A | 9/1988 | Citak et al. |
| 4,865,036 A | 9/1989 | Chirife |
| 5,083,563 A | 1/1992 | Collins |
| 5,129,394 A * | 7/1992 | Mehra .............................. 607/23 |
| 5,188,106 A | 2/1993 | Nappholz et al. |
| 5,195,968 A | 3/1993 | Lundquist et al. |
| 5,203,326 A | 4/1993 | Collins |
| 5,324,326 A | 6/1994 | Lubin |
| 5,334,222 A | 8/1994 | Salo et al. |
| 5,389,090 A | 2/1995 | Fischell et al. |
| 5,464,434 A | 11/1995 | Alt |
| 5,584,868 A | 12/1996 | Salo et al. |
| 5,674,256 A | 10/1997 | Carlson |
| 5,700,283 A | 12/1997 | Salo |
| 5,755,766 A | 5/1998 | Chastain et al. |
| 6,059,778 A | 5/2000 | Sherman |

(Continued)

OTHER PUBLICATIONS

H. Kim and K. Chun. "Integrated MEMS for Pressure Transponder." *Transducers '97*, vol. 2, pp. 1011-1014. Jun. 16, 1997. 1997 International Conference on Solid-Stator Sensor and Actuators. Chicago, IL.

(Continued)

*Primary Examiner* — Niketa Patel
*Assistant Examiner* — Alyssa M Alter
(74) *Attorney, Agent, or Firm* — Brooks, Cameron & Huebsch, PLLC

(57) ABSTRACT

Pacing left and right ventricles of the heart for delivery of heart failure therapy involves measuring right ventricular (RV) pressure and a left ventricular (LV) pressure, and computing a parameter developed from one or both of the RV and LV pressure measurements. The parameter is indicative of a degree of left and right ventricular synchronization. At least one parameter of a heart failure pacing therapy is adjusted based on the parameter to improve synchronization of the right and left ventricles.

20 Claims, 4 Drawing Sheets

(56) References Cited

U.S. PATENT DOCUMENTS

| | | | |
|---|---|---|---|
| 6,066,126 | A | 5/2000 | Li et al. |
| 6,070,100 | A | 5/2000 | Bakels et al. |
| 6,096,036 | A | 8/2000 | Bowe et al. |
| 6,136,021 | A | 10/2000 | Chastain et al. |
| 6,198,952 | B1 | 3/2001 | Miesel |
| 6,198,974 | B1 | 3/2001 | Webster, Jr. |
| 6,221,011 | B1 | 4/2001 | Bardy |
| 6,237,398 | B1 | 5/2001 | Porat et al. |
| 6,270,457 | B1 | 8/2001 | Bardy |
| 6,270,496 | B1 | 8/2001 | Bowe et al. |
| 6,277,072 | B1 | 8/2001 | Bardy |
| 6,280,380 | B1 | 8/2001 | Bardy |
| 6,280,389 | B1 * | 8/2001 | Ding et al. .................... 600/485 |
| 6,280,433 | B1 | 8/2001 | McIvor et al. |
| 6,309,350 | B1 | 10/2001 | VanTassel et al. |
| 6,312,378 | B1 | 11/2001 | Bardy |
| 6,336,903 | B1 | 1/2002 | Bardy |
| 6,358,203 | B2 | 3/2002 | Bardy |
| 6,368,284 | B1 | 4/2002 | Bardy |
| 6,398,728 | B1 | 6/2002 | Bardy |
| 6,398,738 | B1 | 6/2002 | Millar |
| 6,408,214 | B1 | 6/2002 | Williams et al. |
| 6,440,066 | B1 | 8/2002 | Bardy |
| 6,530,914 | B1 | 3/2003 | Mickley |
| 6,628,988 | B2 | 9/2003 | Kramer et al. |
| 6,666,826 | B2 | 12/2003 | Salo et al. |
| 6,853,861 | B1 | 2/2005 | Obel et al. |
| 6,865,419 | B2 * | 3/2005 | Mulligan et al. ................ 607/23 |
| 7,164,948 | B2 | 1/2007 | Struble et al. |
| 7,174,203 | B2 | 2/2007 | Arand et al. |
| 2002/0040010 | A1 | 4/2002 | Rosenzweig et al. |
| 2002/0049478 | A1 | 4/2002 | Ding et al. |
| 2002/0107553 | A1 | 8/2002 | Hill et al. |
| 2003/0130581 | A1 | 7/2003 | Salo et al. |
| 2005/0027323 | A1 | 2/2005 | Mulligan et al. |
| 2005/0043895 | A1 | 2/2005 | Schechter |
| 2006/0293714 | A1 | 12/2006 | Salo et al. |
| 2008/0287818 | A1 | 11/2008 | Shelchuk et al. |

OTHER PUBLICATIONS

Notice of Allowance dated Apr. 7, 2008 from U.S. Appl. No. 10/745,031, 13 pages.
Office Action dated Jan. 23, 2008 from U.S. Appl. No. 10/745,031, 3 pages.
Office Action Response dated Dec. 26, 2007 from U.S. Appl. No. 10/745,031, 16 pages.
Office Action dated Oct. 17, 2007 from U.S. Appl. No. 10/745,031, 10 pages.
Office Action Response dated Aug. 8, 2007 from U.S. Appl. No. 10/745,031, 14 pages.
Office Action dated Jun. 6, 2007 from U.S. Appl. No. 10/745,031, 10 pages.
Office Action Response dated Jan. 30, 2007 from U.S. Appl. No. 10/745,031, 13 pages.
Office Action dated Nov. 1, 2006 from U.S. Appl. No. 10/745,031, 8 pages.
International Search Report dated Apr. 23, 2003 from PCT Application No. PCT/US03/00060, 8 pages.
Office Action dated Oct. 27, 2005 from EP Application No. 03701969.2, 6 pages.
Office Action Response dated May 8, 2006 from EP Application No. 03701969.2, 10 pages.
Office Action dated Sep. 2, 2006 from EP Application No. 03701969.2, 2 pages.
Office Action Response dated Mar. 29, 2007 from EP Application No. 03701969.2, 15 pages.
Notice of Allowance dated Sep. 21, 2007 from EP Application No. 03701969.2, 8 pages.
Pre-Appeal Brief dated May 10, 2010 from U.S. Appl. No. 11/168,024, 5 pages.
Office Action dated Feb. 24, 2010 from U.S. Appl. No. 11/168,024, 4 pages.
Office Action Response dated Feb. 10, 2010 from U.S. Appl. No. 11/168,024, 9 pages.
Office Action Response dated Aug. 12, 2009 from U.S. Appl. No. 11/168,024, 7 pages.
Interview Summary dated Jul. 10, 2009 from U.S. Appl. No. 11/168,024, 2 pages.
Office Action Response dated Mar. 2, 2009 from U.S. Appl. No. 11/168,024, 6 pages.
Office Action dated Feb. 26, 2009 from U.S. Appl. No. 11/168,024, 4 pages.
Office Action Response dated Sep. 22, 2008 from U.S. Appl. No. 11/168,024, 18 pages.
Office Action Response dated Jun. 6, 2008 from U.S. Appl. No. 11/168,024, 15 pages.
Office Action Response dated Dec. 26, 2007 from U.S. Appl. No. 11/168,024, 12 pages.
International Preliminary Report on Patentability dated Jan. 17, 2008 from PCT Application No. PCT/US2006/025524, 9 pages.
Office Action Response dated Feb. 25, 2010 from European Application No. 06774332.8, 3 pages.
Office Action from U.S. Appl. No. 11/168,024 dated Dec. 10, 2009, 10 pages.
Office Action from U.S. Appl. No. 11/168,024 dated Jun. 1, 2009, 11 pages.
Office Action from U.S. Appl. No. 11/168,024 dated Oct. 29, 2008, 12 pages.
Office Action from U.S. Appl. No. 11/168,024 dated Jul. 22, 2008, 13 pages.
Office Action from U.S. Appl. No. 11/168,024 dated Apr. 2, 2008, 12 pages.
Office Action from U.S. Appl. No. 11/168,024 dated Sep. 24, 2007, 12 pages.
Appeal Brief dated Sep. 20, 2010 from U.S. Appl. No. 11/168,024, 20 pages.
Office Action dated Dec. 22, 2010 from U.S. Appl. No. 11/168,024, 10 pages.
File History for U.S. Appl. No. 11/168,024.
Office Action dated Dec. 5, 2011 from Japanese Application No. 2008-519599, 8 pages (with translation).
Office Action Response dated Jun. 5, 2012 from Japanese Application No. 2008-519599, 7 pages.

* cited by examiner

HEART FAILURE THERAPY ADJUSTMENT BASED ON VENTRICULAR PRESSURES

RELATED PATENT DOCUMENTS

This application is a continuation of patent application Ser. No. 10/745,031, filed on Dec. 23, 2003, to issue as U.S. Pat. No. 7,409,244, which is a divisional of patent application Ser. No. 10/038,936, filed on Jan. 4, 2002, and now issued as U.S. Pat. No. 6,666,826, which are hereby incorporated herein by reference.

FIELD OF THE INVENTION

The invention relates to a method and apparatus for pacing the left and right ventricles in response to a hemodynamic parameter computed using one or both of left and right ventricular blood pressure measurements.

BACKGROUND OF THE INVENTION

Heart disease (cardiomyopathy) can cause a patient to exhibit symptoms of congestive heart failure (CHF). CHF is a result of the weakening of the heart's cardiac function characterized by reduced pumping capacity and efficiency. Chronic cardiac rhythm problems can also be the result of cardiomyopathy. The modification of the heart's structure that causes the reduction in pumping capacity also causes modification of the heart's electrical characteristics. The heart's electrical pathways can become stretched out of shape and chemically damaged. This makes arrhythmias much more likely to occur in CHF patients.

Implantation of a pacemaker is a preferred method of treatment for arrhythmias in CHF patients. Although many types of heart problems may require a pacer, one method of treatment suited for CHF patients is known as cardiac resynchronization therapy (CRT). CRT uses a pacemaker with multiple pacing leads to coordinate the heart's four chambers to act together in a sequence that will pump blood more efficiently.

It is likely that CRT candidates will have various forms of cardiomyopathy, and these patients may exhibit other measurable symptoms of reduced cardiac function besides arrhythmia. The reduced cardiac function of the heart is taken into account when applying CRT in order to tailor the treatment based on the needs of a particular patient. Various external factors must also be taken into account by the pacing system, one of those factors being the current state of activity of the patient.

Rate adaptive pacemakers are currently used that can estimate body activity by detecting body activity or breathing rate and depth, and therefore modify the pacing rate applied to the heart. These indicators can give a rough estimate of metabolic demand for a given patient. It would be beneficial to have more accurate measures of metabolic demand, especially measures that can determine the pumping capacity and pumping efficiency of a heart in order to measure and improve the efficacy of the therapy for the CHF patient.

For the reasons stated above, and for other reasons stated below which will become apparent to those skilled in the art upon reading the present specification, there is a need in the art for improved ventricular monitoring and therapy control. There exists a further need for a pacing system that provides a means of measuring cardiac workload and efficiency in order to offer more effective treatment for CHF patients. The present invention fulfills these and other needs, and provides several advantages over prior systems and techniques.

SUMMARY OF THE INVENTION

The present invention is directed to a method and apparatus for pacing left and right ventricles of the heart, particularly in the context of a patient having a heart failure condition. Embodiments of the invention are directed to pacing left and right ventricles of the heart for delivery of heart failure therapy, which involve measuring right ventricular (RV) pressure and a left ventricular (LV) pressure, and computing a parameter developed from the RV and LV pressure measurements. The parameter is preferably derived from a comparison of the RV and LV pressure measurements, and is indicative of a degree of left and right ventricular synchronization. At least one parameter of a heart failure pacing therapy is adjusted based on the parameter to improve synchronization of the right and left ventricles.

According to other embodiments, methods of pacing the right and left ventricles involve measuring one or both of a right ventricular (RV) pressure and a left ventricular (LV) pressure, and computing a parameter developed from the one or both of the RV and LV pressure measurements. The parameter is indicative of a degree of left and right ventricular synchronization. The method further involves assessing the parameter, and adjusting at least one heart failure pacing therapy parameter (e.g., atrioventricular delay, interventricular delay) based on the parameter assessment. The at least one pacing parameter is adjusted to improve synchronization of the right and left ventricles. The computed parameter is a parameter indicative of hemodynamic state, such as a PP Loop or a pre-ejection period. The pacing parameter is preferably adjusted to reduce an area of the PP Loop or reduce the pre-ejection period.

Assessing the parameter indicative of the degree of left and right ventricular synchronization may involve patient-externally assessing the parameter. Assessing the computed parameter and adjusting the pacing parameter may be performed during physician monitoring of a heart failure condition. Assessing the computed parameter and pacing parameter may further be performed during a therapy for treating a heart failure condition.

According to another embodiment, an apparatus for pacing the right and left ventricles includes a lead system comprising a right ventricular (RV) lead and a left ventricular (LV) lead. A pressure sensor system of the apparatus includes one or both of a left ventricular pressure (LVP) sensor catheter and a right ventricular pressure (RVP) sensor catheter. A telemetry circuit is disposed in an implantable housing and configured to communicate with a patient-external device. A processor, disposed in the housing, is coupled to the telemetry circuit and to the lead and pressure sensor systems. The processor computes a parameter developed from a pressure measurement made by the pressure sensor system. The parameter is indicative of a degree of left and right ventricular synchronization. The processor, in response to assessment of the parameter, adjusts a heart failure therapy pacing parameter to improve synchronization of the right and left ventricles.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
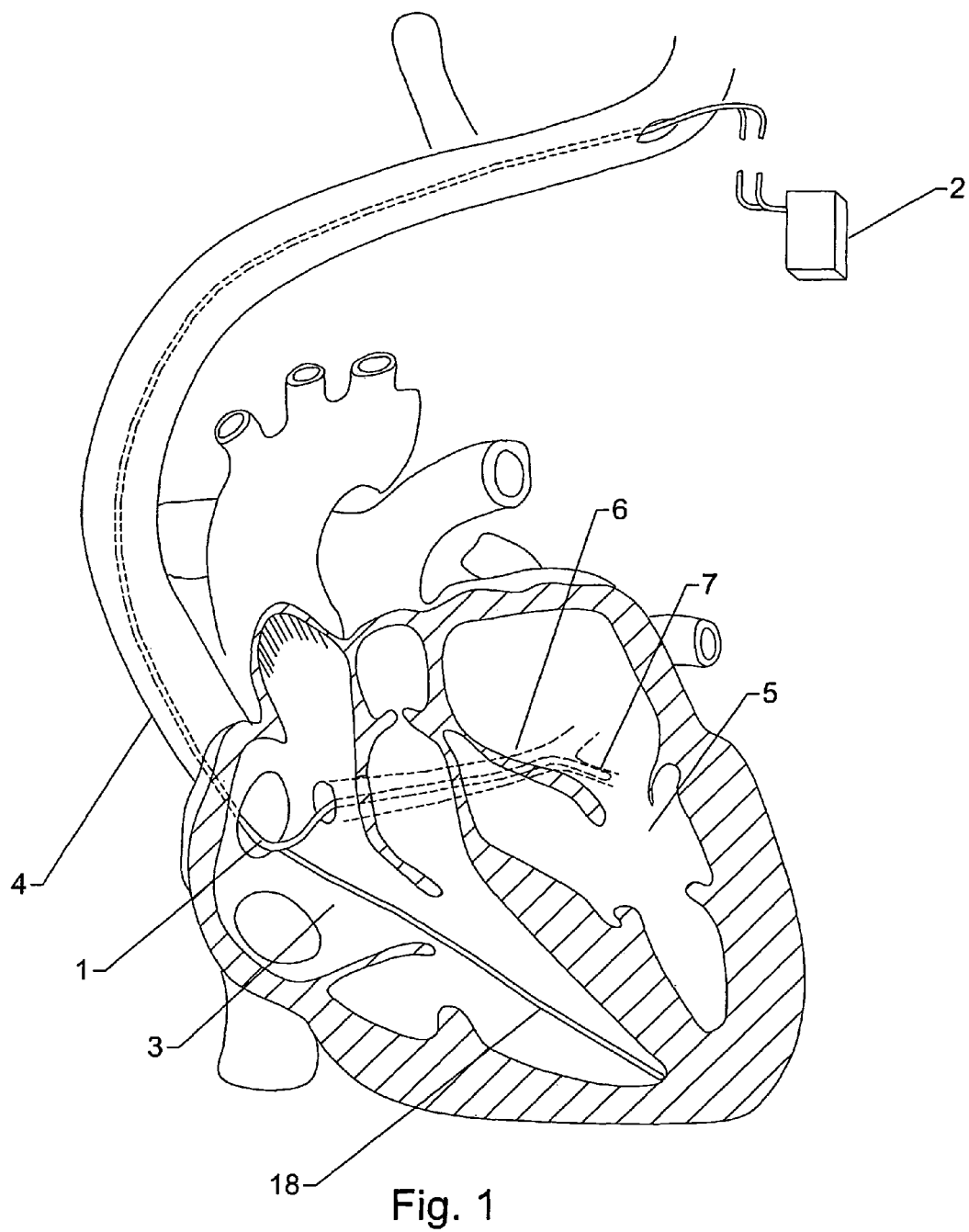
FIG. 1 is a view of the heart showing an apparatus according to the present invention implanted in the coronary sinus.

While the invention is amenable to various modifications and alternative forms, specifics thereof have been shown by way of example in the drawings and will be described in detail herein. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

Various measures have been developed to characterize reduced cardiac function. One such measure is hemodynamic state, which can be loosely defined as the physics of blood flow in the circulation system. Estimating hemodynamic state includes measuring physical properties of blood such as pressure and temperature. The measurements can be taken from various chambers within the heart, including the left and right ventricles.

Hemodynamic measurements from the left ventricle are considered particularly useful, although placing devices in the left ventricle or within myocardial tissue is considered risky. Thrombus formed on implanted devices can break loose and travel to the brain causing a stroke or blockage of other blood vessels. The relatively high pressure in the left ventricle also poses the risk of hemorrhage at penetration points of the implanted device.

Given that hemodynamic parameters can be useful and accurate indicators of heart performance, the hemodynamic parameters can be beneficially applied to adaptively change therapy parameters, for example, of a cardiac pacing or defibrillation system. Further, analyzing hemodynamic state can provide a pacing system with the ability to measure and adapt to heart activity over a long period of time in order to measure and improve the efficacy of the pacing treatment for the CHF patient.

A system according to the present invention uses a pressure reading obtained from a coronary vein in the left ventricle to provide an estimate of left ventricular pressure (LVP). The LVP is generally much more indicative of cardiac function than right ventricular pressure. The left ventricular end diastolic pressure (LVEDP) is an especially important measure used to evaluate hemodynamic state. LVEDP can be measured from a coronary vein without exposing the patient to the risks involved in obtaining direct readings from the left ventricle or left atrium.

Turning now to FIG. 1, a system according to the present invention is shown deployed within a heart. The system includes a lead system 1 that is designed for implantation in a coronary vein for purposes of cardiac resynchronization therapy (CRT). The lead system 1 is coupled to a detection/energy delivery system 2 that actively measures and controls the implanted lead system to correct for electrical activation anomalies of the heart.

The detector/energy delivery system 2 typically includes a power supply and programmable circuit (e.g., microprocessor) coupled to an analog to digital (A-D) converter. Various lead system devices, such as electrodes and pressure sensors, can interface to the A-D converter for sensing/data collection. Alternatively, analog conditioning (e.g., filtering) may be applied to sensor signals before interfacing with the A-D converter. The detector/energy delivery system 2 also utilizes an energy delivery system. The energy delivery system may include charge capacitors and signal conditioning circuitry known in the art. The energy system may interface to the programmable circuit through a D-A converter.

A system according to the present invention may also be adapted for monitoring purposes only, in which case the detector/energy delivery system 2 may not require an energy delivery system. Further, although the detector/energy delivery system 2 is typically implantable, it can be appreciated that a detector/energy delivery system 2 can be externally located, in whole or in part, in some applications, such as for a temporary installation or in clinical testing.

The lead system 1 is implanted into the coronary sinus using various techniques. One such technique, as illustrated in FIG. 1, involves creating an opening in a percutaneous access vessel such as the left subclavian or left cephalic vein. The pacing lead is guided into the right atrium 3 of the heart via the superior vena cava 4. From the right atrium 3, the lead system 1 is sent into the coronary sinus ostium. The ostium is the opening of the coronary sinus 6 into the right atrium 3. The lead system 1 is guided through the coronary sinus 6 to a coronary vein 7 of the left ventricle 5. A distal end of the lead system 1 is lodged into the coronary vein 7.

Figure 2:
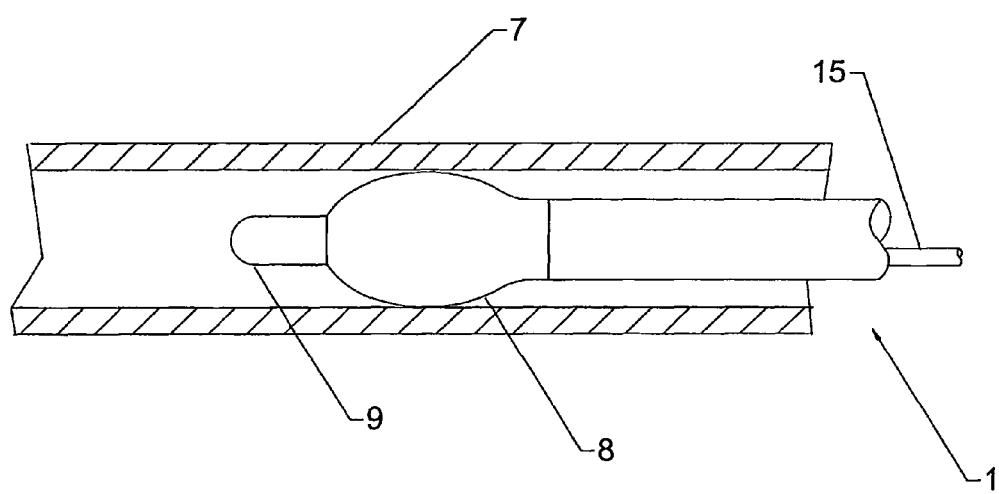
FIG. 2 is a view of a system according to the present invention implanted in a coronary vein.

As illustrated in FIG. 2, the lead system 1 is lodged in position such that the lead system 1 can occlude blood flow in the coronary vein 7. Blood flow can be occluded in the coronary vein 7 to ensure that a pressure transducer 9 obtains a hydrostatic pressure of blood in the coronary vein 7.

To enable occlusion, the lead system 1 includes an occlusion device 8 that is located on a distal end of the lead system 1. Depending on the venous implantation path and any guide assistance apparatus used in the implantation procedure, the occlusion device 8 may include an enlarged diameter of the distal end. An enlarged diameter is formed with dimensions such that it can successfully occlude the coronary vein 7 while still allowing the lead system 1 to be advanced unimpeded along the implantation path.

In cases where an enlarged diameter of the lead system 1 cannot be used to occlude the coronary vein 7, alternate configurations of the occlusion device 8 may be used. Alternate occlusion devices 8 include an agent that swells upon fluid contact applied at a distal end of the lead system 1. Absorbable embolic agents such as Gelfoam (gelatin sponge) or Avitene (microfibrillar collagen) can be applied around the periphery of the distal end of a lead system 1 to provide occlusion. The absorbable agent can be combined with a non-absorbable agent such as polyvinyl alcohol (PVA) particles to increase adhesion. Other configurations of an occlusion device 8 may include an inflatable balloon. A balloon can be mounted on the distal end of the lead system 1 and inflated by injection of a fluid within an open lumen of the lead system 1.

The lead system 1, as shown in FIG. 2, includes a pressure transducer 9 at a distal tip. A pressure transducer 9 used in this application can be a micro-electrical-mechanical system (MEMS). MEMS technology uses semiconductor techniques to build microscopic mechanical devices in silicon or similar materials. The pressure transducer 9 can include a micromachined capacitive or piezoresistive transducer exposed to the bloodstream. Other pressure transducer technologies, such as resistive strain gages, are known in the art and can also be employed as a pressure transducer 9. The pressure transducer 9 is coupled to one or more conductors 15 disposed along the length of the lead system 1. In the configuration shown in FIG. 2, the pressure transducer 9 is integrated with the lead system 1.

Figure 3:
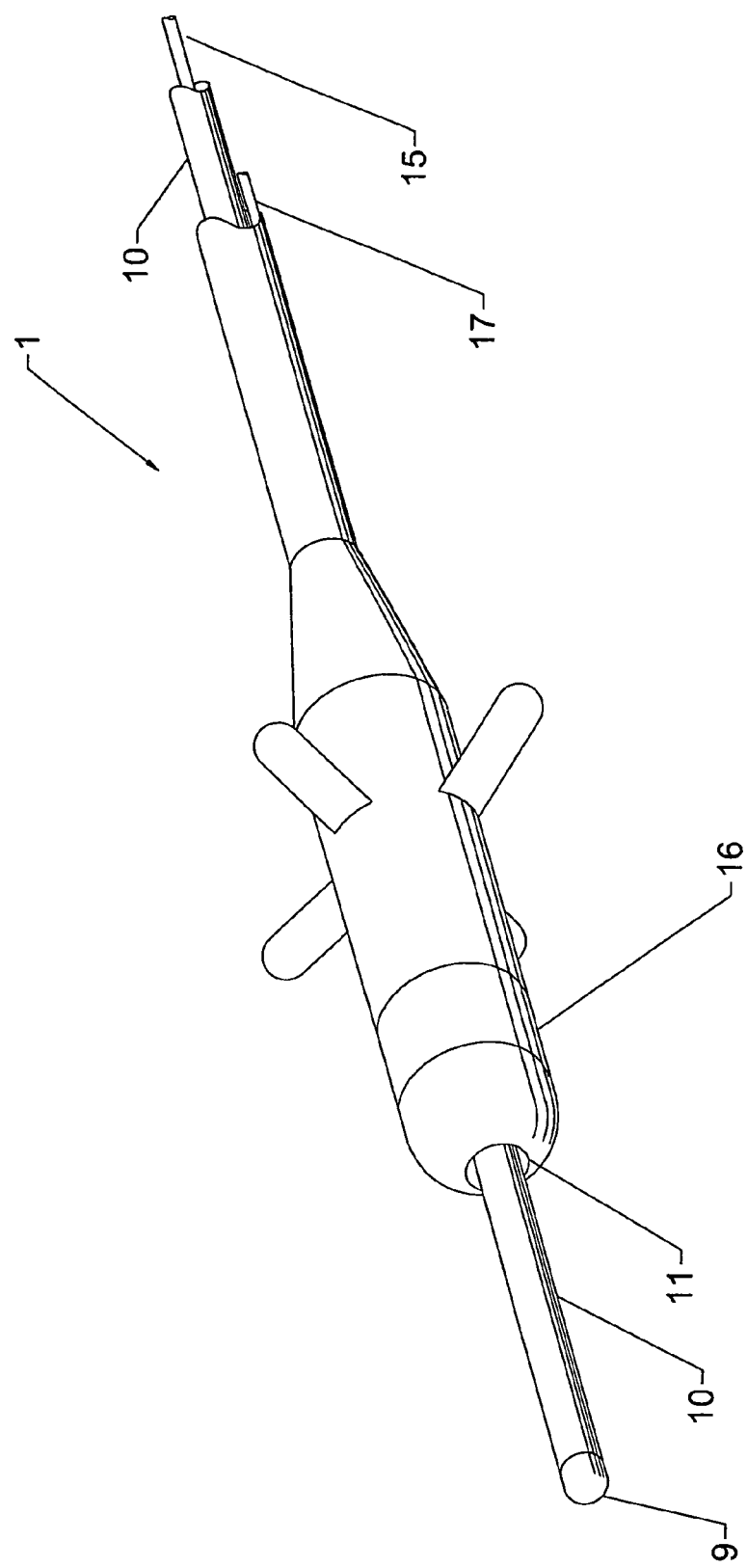
FIG. 3 is an external view of a distal end of an apparatus embodying features of the present invention.

FIG. 3 shows an alternate configuration of a pressure transducer 9. The pressure transducer 9 is mounted to a distal tip of a catheter 10. The catheter 10 is sized such that it can be movably disposed within an open lumen 11 of the lead system 1. The lead system 1 may already include an open lumen 11 for an over-the-wire installation technique. After lead system installation, the catheter 10 can be distally advanced through the lead system 1 until a distal tip of the catheter 10 extends past the distal tip of the lead system 1. This advantageously allows the orientation of the transducer 9 to be adjusted during installation to account for effects such as damping caused by nearby anatomical features. After the catheter 10 has been positioned satisfactorily, it can be secured to the lead system 1 and coupled to the detection/energy delivery system 2 (shown in FIG. 1).

At least one electrode 16 is also disposed on a distal end of the lead system 1. The electrode 16 is utilized to read electrical signals from the heart and apply synchronized electrical impulses to the heart tissue to pace the heart. The electrode is coupled to a conductor 17. In one configuration, two or more electrodes 16 are utilized, with one electrode 16 used for reading electrical signals while other electrodes 16 are used for applying electrical impulses. Construction and use of pacing lead electrodes 16 are well known in the art.

In a system according to the present invention, the electrical impulses delivered to the electrode 16 can be adaptively adjusted by the detection/energy delivery system 2 based on pressure sensor outputs from the pressure transducer 9. This adjustment of the impulses may include a change of pacing rate (e.g., to adapt to changes in activity) or may include a change in the synchronization of electrical signals used to provide CRT (e.g., when reduced pumping capacity is detected).

Figure 4:
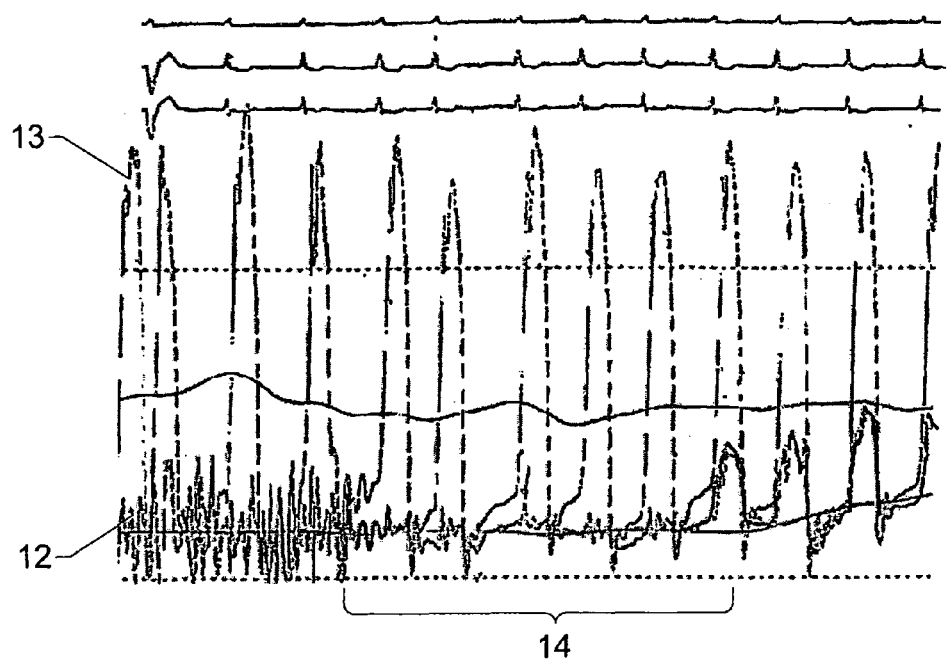
FIG. 4 is an ECG and pressure graph showing a pressure reading from a device according to the present invention overlaid with left ventricular pressure readings, the graph showing the change in coronary vein pressure before and after vein occlusion.

The pressure readings from the pressure transducer 9 in the occluded coronary vein 7 are proportional to LVP. FIG. 4 shows the pressure 12 measured from the coronary vein using a device according to the present invention. The LVP 13 from the same heart is also shown in FIG. 4. Occlusion of the coronary vein occurs in the region 14 shown in FIG. 4. Note that prior to occlusion, the coronary vein pressure 12 is random, corresponding to dynamic pressure of turbulent flow within the vein. After occlusion, the pressure 12 is a hydrostatic pressure reading that is proportional to the LVP 13.

Figure 5:
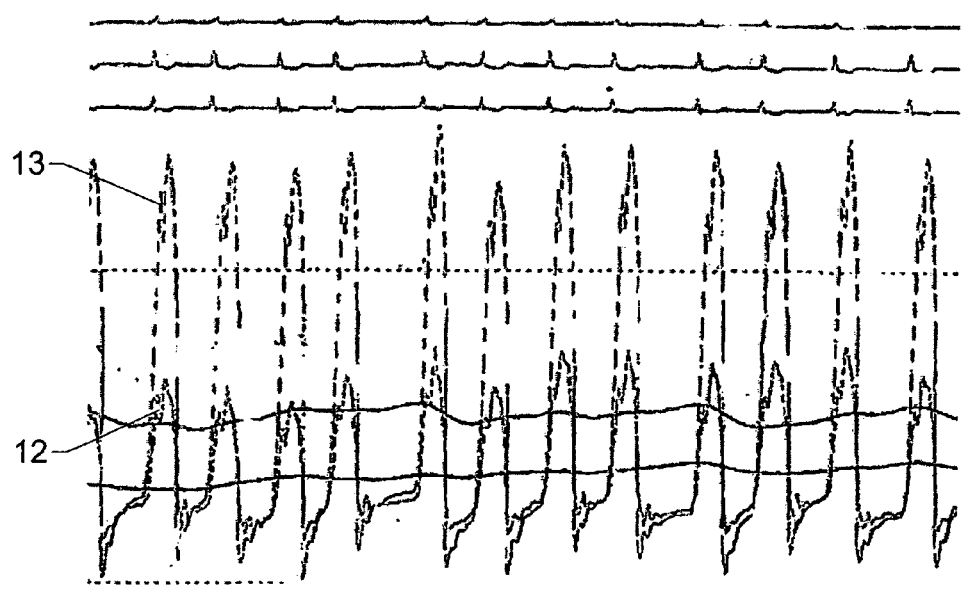
FIG. 5 is an ECG and pressure graph showing a steady-state pressure reading from a device according to the present invention overlaid with direct left ventricular pressure readings.

In FIG. 5, a steady state, hydrostatic, coronary vein pressure 12 is shown superimposed over the LVP 13. The amplitude of the coronary vein pressure 12 is proportional to the LVP 13. The coronary vein pressure 12 faithfully reproduces timing and amplitude variations of the left ventricle systolic pressure. In cases where actual LVP 13 values are desired, the reading of coronary vein pressure 12 can be adjusted with a scaling factor. The scaling factor can be determined after lead installation by using a cuff reading or by using an invasive arterial method to measure actual LVP 13. The measured LVP 13 is compared versus coronary vein pressure 12 to derive the scaling factor. The scaling factor can be input to the detection/energy delivery system 2 and used for processing of pressure transducer readings.

Measuring LVP with a device according to the present invention provides other benefits for applying CHF therapies. For example, in cardiac therapy using bi-ventricular pacing (e.g., CRT), benefits are obtained from synchronizing the contractions of the right and left ventricle using pacing electrodes. If a method or apparatus for acquiring a right ventricular pressure (RVP) signal is provided (for example, via a pressure transducer incorporated into a right ventricular pacing lead) and the left ventricular pressure signal is acquired from a coronary venous lead, the degree of synchronization of these two chambers can be assessed by plotting RVP versus the LVP and determining the area of the resulting approximately elliptical shape. This elliptical shape is referred to as a PP Loop.

A method and apparatus for using the PP Loop for characterizing therapy for CHF patients is described in commonly owned U.S. Pat. No. 6,280,389, which is hereby incorporated herein by reference. A given parameter (e.g., atrioventricular delay or interventricular delay) associated with CRT may be optimized by varying the parameter(s) to minimize the PP Loop area. This process can be carried out periodically to correct for physiological changes which may occur in the course of the disease or therapy. Alternatively, these parameters may be adjusted to generate a desired time or phase delay between the right and left ventricular pressure signals. The relative timing or phase of these pressure signals may be extracted by analysis of maximum or minimum threshold values from time domain pressure readings. Relative phasing can also be determined from the frequency domain by analyzing the fundamental of a Fourier analysis, such as by use of a Fast Fourier Transform (e.g., FFT) analysis. The computation required to perform FFT and/or extract timing values from pressure signals is known in the art and can be readily implemented in the detector/energy delivery system 2.

Referring back to FIG. 1, an exemplary second lead system 18 for measuring right ventricular pressure is shown deployed in the right ventricle. The second lead system 18 can include pressure transducers and electrodes similar to the configurations described for the lead system 1. The second lead system 18 is coupled to the detector/energy delivery system 2, and can provide RVP readings useful for deriving a PP Loop. The second lead system 18 can also sense and deliver electrical signals useful for therapies such as CRT.

Another benefit provided by the present invention relates to the ability to provide electromechanical timing. Electromechanical timing may be continuously assessed by measuring the time interval between an electrical event (for example, the beginning of an R-wave) and a mechanical event such as the beginning of an increase in LVP measured with a coronary venous pressure transducer during isovolumic contraction. This interval, called the pre-ejection period or PEP, is related to sympathetic nervous activation and may be used to control pacing rate or other CRT parameters (e.g., atrioventricular delay or interventricular delay). An apparatus for controlling pacing parameters based on PEP is described in commonly owned U.S. Pat. No. 4,773,401, which is hereby incorporated herein by reference.

A system according to the present invention can provide improved therapy by adjusting pacing parameters to minimize the PEP. When the isovolumic contraction time, which is the variable component of the PEP, reaches a minimum value, the left ventricular mechanical activation is occurring in the most synchronous fashion and the contraction is, therefore, most mechanically efficient. This optimization is ideally carried out at rest under otherwise steady state conditions because variations in PEP due to activation of the sympathetic nervous system could confuse the outcome.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. An apparatus for pacing right and left ventricles of a heart for delivery of a heart failure pacing therapy, comprising:
    a lead system comprising a right ventricular (RV) lead and a left ventricular (LV) lead;
    a pressure sensor system comprising a left ventricular pressure (LVP) sensor and a right ventricular pressure (RVP) sensor, the RVP sensor configured to take an RV pressure measurement and the LVP sensor configured for placement in the coronary sinus or a coronary vein and to measure a coronary sinus pressure or a coronary vein pressure which is proportionally related to an LV chamber pressure;
    an implantable housing;
    a telemetry circuit disposed in the housing and configured to communicate with a patient-external device; and
    a processor disposed in the implantable housing, the processor coupled to the telemetry circuit and to the lead and pressure sensor systems, the processor configured to execute program instructions stored in memory to compute at least one parameter based at least in part on a comparison of RVP and LVP sensor pressure measurements wherein the parameter is indicative of a degree of left and right ventricular synchronization, the processor configured to adjust the at least one parameter of the heart failure pacing therapy to improve synchronization of the right and left ventricles based on the at least one computed parameter.

2. The apparatus of claim 1, wherein the processor is configured to apply a scaling factor to the LVP sensor pressure measurement to compute an actual LV chamber pressure value.

3. The apparatus of claim 1, wherein the at least one parameter of the heart failure pacing therapy comprises an atrioventricular delay.

4. The apparatus of claim 1, wherein the at least one parameter of the heart failure pacing therapy comprises an interventricular delay.

5. The apparatus of claim 1, wherein the at least one parameter of the heart failure pacing therapy comprises an atrioventricular delay and an interventricular delay.

6. The apparatus of claim 1, wherein the LVP sensor is movably disposed within an open lumen of the LV lead, a distal tip of the LVP sensor extendable beyond a distal tip of the LV lead, the LVP sensor comprising at least one pressure transducer at a distal end of the LVP sensor.

7. The apparatus of claim 1, wherein the lead system comprises an occlusion device at a distal end of the LVP sensor, and the LVP sensor senses hydrostatic pressure.

8. The apparatus of claim 1, wherein the processor is configured to adjust the at least one parameter of the heart failure pacing therapy to obtain a desired time or phase delay between signals produced by the RVP and LVP sensor.

9. The apparatus of claim 1, wherein the processor is configured to adjust the at least one parameter of the heart failure pacing therapy to optimize synchronization of the right and left ventricles.

10. The apparatus of claim 1, wherein the processor is configured to adjust the at least one parameter of the heart failure pacing therapy to reduce an area of a PP Loop developed from the comparison of the RVP and LVP sensor pressure measurements.

11. The apparatus of claim 1, wherein the processor is configured to repeatedly execute the program instructions over time to correct for physiological changes which may occur in the course of disease progression or disease treatment.

12. An apparatus for pacing right and left ventricles of a heart for delivery of a heart failure pacing therapy, comprising:
    a lead system comprising a right ventricular (RV) lead and a left ventricular (LV) lead;
    a pressure sensor system comprising a left ventricular pressure (LVP) sensor and a right ventricular pressure (RVP) sensor, the RVP sensor configured to take an RV pressure measurement and the LVP sensor configured for placement in the coronary sinus or a coronary vein and to measure a coronary sinus pressure or a coronary vein pressure which is proportionally related to an LV chamber pressure;
    an implantable housing;
    a telemetry circuit disposed in the housing and configured to communicate with a patient- external device;
    means for computing at least one parameter based at least in part on a comparison of RVP and LVP sensor pressure measurements wherein the parameter is indicative of a degree of left and right ventricular synchronization; and
    means for adjusting the at least one parameter of the heart failure pacing therapy to improve synchronization of the right and left ventricles based on the at least one computed parameter.

13. The apparatus of claim 12, further comprising means for applying a scaling factor to the LVP sensor pressure measurement to determine an actual LV chamber pressure value.

14. The apparatus of claim 12, wherein the at least one parameter of the heart failure pacing therapy comprises an atrioventricular delay.

15. The apparatus of claim 12, wherein the at least one parameter of the heart failure pacing therapy comprises an interventricular delay.

16. The apparatus of claim 12, wherein the at least one parameter of the heart failure pacing therapy comprises an atrioventricular delay and an interventricular delay.

17. The apparatus of claim 12, wherein the lead system comprises an occlusion device at a distal end of the LVP sensor, and the LVP sensor senses hydrostatic pressure.

18. The apparatus of claim 12, further comprising means for adjusting the at least one parameter of the heart failure pacing therapy to obtain a desired time or phase delay between signals produced by the RVP and LVP sensors.

19. The apparatus of claim 12, further comprising means for adjusting the at least one parameter of the heart failure pacing therapy to optimize synchronization of the right and left ventricles.

20. The apparatus of claim 12, further comprising means for adjusting the at least one parameter of the heart failure pacing therapy to reduce an area of a PP Loop developed from the comparison of the RVP and LVP sensor pressure measurements.

* * * * *